United States Patent [19]

Gewartowski

[11] 4,129,606
[45] Dec. 12, 1978

[54] TEMPERATURE CONTROL OF INTEGRATED FRACTIONATION COLUMN AND REACTION ZONE

[75] Inventor: Steve A. Gewartowski, Mt. Prospect, Ill.

[73] Assignee: UOP Inc., Des Plaines, Ill.

[21] Appl. No.: 826,909

[22] Filed: Aug. 22, 1977

Related U.S. Application Data

[63] Continuation-in-part of Ser. No. 762,220, Jan. 24, 1977, Pat. No. 4,053,367, which is a continuation-in-part of Ser. No. 717,978, Aug. 26, 1976, Pat. No. 4,024,026.

[51] Int. Cl.² ............................ C07C 7/01; C07C 5/24
[52] U.S. Cl. ..................................... 260/674 R; 203/2; 203/23; 203/41; 203/DIG. 18; 208/260; 208/DIG. 1; 260/668 A; 260/671 R; 260/672 R; 260/672 T; 260/683.2; 260/683.65
[58] Field of Search ............... 203/2, 23, 41, DIG. 18; 208/DIG. 1, 260, 668 A, 672 R, 672 T; 260/674 SA, 674 R, 671 R, 683.2, 683.65

[56] References Cited

U.S. PATENT DOCUMENTS 4,024,026  5/1977  Gewartowski .............. 260/674 SA
4,053,367  10/1977  Gewartowski .............. 260/674 R Primary Examiner—Delbert E. Gantz
Assistant Examiner—C. E. Spresser
Attorney, Agent, or Firm—James R. Hoatson, Jr.; John F. Spears, Jr.; William H. Page, II

[57] ABSTRACT

A hydrocarbon stream comprising $C_2$ to $C_8$ hydrocarbons is stripped at a high temperature to allow passage of the stripper bottoms stream into a reaction zone without further heating, and the effluent of the reaction zone is then heat exchanged against the feed stream to the stripper column to recover heat. Operation of the reaction zone at the desired temperature is achieved by adjusting the amount of the stripper bottoms stream which is split off for cooling by heat exchange against the feed to the stripper column. The cooled split-off portion is then admixed with the remaining high temperature portion. Adjusting the flow rate of the portion of hot reaction zone effluent which is heat exchanged against the stripper feed stream is performed to control either the temperature of the stripper feed stream or the temperature of the reaction zone effluent as it is passed to a downstream operation.

7 Claims, 1 Drawing Figure

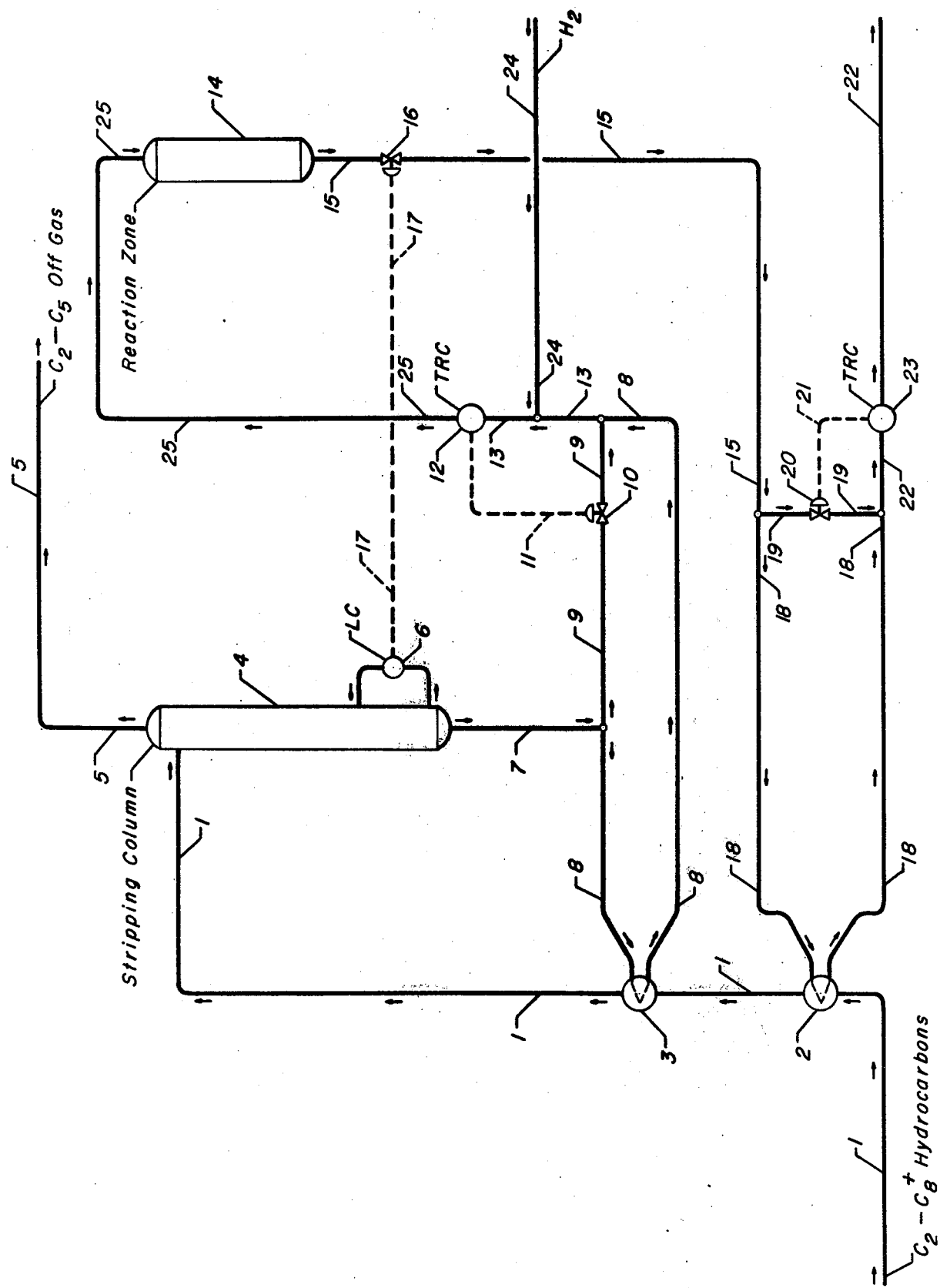

TEMPERATURE CONTROL OF INTEGRATED FRACTIONATION COLUMN AND REACTION ZONE

CROSS-REFERENCE TO RELATED APPLICATIONS

This application is a continuation-in-part of my co-pending prior application Ser. No. 762,220, filed Jan. 24, 1977, now U.S. Pat. No. 4,053,367, which was a continuation-in-part of my prior application Ser. No. 717,978, filed Aug. 26, 1976 and now U.S. Pat. No. 4,024,026. The teachings of my prior applications are incorporated herein by reference.

FIELD OF THE INVENTION

The invention relates to a temperature control method for use on a hydrocarbon conversion process which involves the sequential fractionation and low temperature reaction of the hydrocarbons. The invention more specifically relates to the integration of the heat exchange used in connection with a stripping column and a downstream reaction zone through which the hydrocarbons are passed in sequence. The reaction zone is preferably a hydrotreating or isomerization zone.

PRIOR ART

The various reaction zones and fractionation zones referred to herein are well developed and are used commercially. Furthermore, in many hydrocarbon conversion processes it is a common practice to heat the feed stream to a reaction zone by indirect heat exchange against another process stream including the effluent of the reaction zone. It is also an accepted practice to recover heat from the effluent of a reaction zone by indirect heat exchange.

As the subject invention is directed to a control method similar to that of my prior application which relates to clay treating, it is believed that the prior art relating to clay treating remains relevant. It is normally the heavier hydrocarbons, that is those having six or more carbon atoms per molecule, which are subjected to clay treating rather than lighter hydrocarbons. This segregation is often accomplished by fractional distillation. A common flow scheme therefore consists of the passage of a reaction zone effluent stream into a stripping column followed by passage of the bottoms stream of the stripping column through a clay treating zone. This is illustrated in U.S. Pat. No. 3,754,045 (Cl. 260-672NC). This reference teaches the passage of the stripping column bottoms directly into the clay treating zone and is concerned with the hydrodealkylation of toluene. The effluent of the clay treating zone is passed into a benzene column. U.S. Pat. No. 2,733,286 (Cl. 260-674) illustrates the clay treatment of a benzene-rich intermediate fraction derived from a thermally cracked heavy naphtha or gas oil. The effluent of this clay treating zone is then passed into a fractionation column used to remove the heavy polymers formed by the polymerization of olefins and diolefins in the clay treating zone.

Another of the common flow schemes utilizing distillation followed by clay treating is shown in U.S. Pat. No. 2,775,632 (Cl. 260-674). In this process, a naphtha is subjected to a reforming operation and the reformate is separated by liquid-liquid extraction to produce a stream rich in aromatic hydrocarbons. This stream is dried, typically by distillation, clay treated and then distilled for the removal of polymers. The result is a nitration grade aromatic product. This reference teaches the use of a temperature of from 275° F. to 375° F. and a pressure sufficient to maintain liquid phase conditions in the clay treating zone. Previously cited U.S. Pat. No. 2,733,286 increases the range of suitable clay treating temperatures to 250° F. to 400° F., and U.S. Pat. No. 3,835,037 (Cl. 208-260) lowers the bottom limit of the range to about 203° F. to 257° F.

Other references illustrating the arts of hydrocarbon separation and fractionation control are U.S. Pat. Nos. 3,434,934 (Cl. 202-154); 3,446,709 (Cl. 193-132) and 3,555,837 (Cl. 62-17).

Heretofore, the bottoms stream of the stripping column was not bifurcated into two streams, and one of these streams was not cooled and then remixed with the other to adjust the inlet temperature of a downstream reaction zone. In the prior art systems, this bottoms stream is heated or cooled as needed as an entity.

Some representative examples of the prior art of hydrotreating are provided by U.S. Pat. Nos. 3,537,982 (Cl. 208-255); 3,537,981; 3,215,618 (Cl. 208-143); 3,725,252 (Cl. 208-213); 3,700,586 (Cl. 208-89); 3,726,788 and 3,491,019. U.S. patents directed to hydrocarbon isomerization processes include U.S. Pat. Nos. 2,938,936 (Cl. 260-683.68); 3,112,351 (Cl. 260-683.75); 3,128,319; 3,283,021; 3,652,697; 3,755,144 (Cl. 208-95) and 3,821,123 (Cl. 252-439). These references are relevant for their showing of representative catalyst compositions, operating conditions, feedstocks and flow schemes.

BRIEF SUMMARY OF THE INVENTION

The invention provides a method of controlling the inlet temperature of a stream of hydrocarbons fed to a reaction zone from the bottom of a fractionation column. The invention also provides a system for adjusting the temperature of the reaction zone effluent stream before it is passed into the next processing step or of adjusting the temperature of the feed stream to the fractionation column.

One method of the subject invention comprises the steps of removing a bottoms stream from the stripping column while it is operated with a bottom temperature in excess of the maximum desired inlet temperature of the reaction zone, cooling this bottoms stream by first dividing it into two portions and cooling one portion by heat exchange against the feed stream to the stripping column and then recombining the two portions of the bottoms stream, measuring the resultant lower temperature of the bottoms stream and comparing the measured temperature to the then desired inlet temperature of the reaction zone, and adjusting the relative flow rates of the first portion and the second portion of the bottoms stream in a manner which changes the measured temperature to the desired inlet temperature. The recombined bottoms stream is then passed into the reaction zone, and the desired inlet temperature of the reaction zone is gradually increased during the useful life of the catalyst until some maximum temperature is reached. The remaining steps in the subject method include cooling the reaction zone effluent stream by first dividing it into two portions and cooling one portion by heat exchange against the feed stream to the stripping column and then recombining the two portions of the reaction zone effluent stream, measuring the resultant lower temperature of the reaction zone effluent stream and comparing the measured temperature to the then desired inlet temperature of the processing operation next downstream of the reaction zone, and adjusting the relative flow rates of the first portion and the second portion of the reaction zone effluent stream in a manner which changes the measured temperature to the desired inlet temperature. Other embodiments of the invention are described herein and include the division of the reaction zone effluent stream according to the temperature of the feed stream to thereby regulate the temperature of the feed stream as it enters the stripping column.

DESCRIPTION OF THE DRAWING

The drawing illustrates the preferred embodiment of the invention. It is assumed that a mixture of $C_2$ to $C_8$ or heavier hydrocarbons is charged through line 1 and heat exchanged against a reaction zone effluent stream in a first or feed-effluent heat exchanger 2. It is then further heated by passage through a second heat exchanger 3 and passed into a stripping column 4. This column is operated with a bottom temperature which is maintained above the maximum desired inlet temperature of the reaction zone 14 by a reboiler system which is not shown. An overhead vapor stream containing essentially all of the $C_1$ to $C_5$ hydrocarbons in the feed stream and a very minor amount of $C_6$ hydrocarbons is removed from the stripping column in line 5.

A bottoms stream comprising $C_6$ and heavier hydrocarbons is removed from the stripping column in line 7 and is divided into a first portion which passes through line 9 at a rate controlled by valve 10 and a second portion which passes through line 8. The rate of flow of the bottoms stream in transfer line 7 is preferably controlled through use of a valve means 16 located downstream of the reaction zone 14. This valve is actuated by a signal carried by means 17 in response to a level control system 6 in the bottom of the stripping column. The second portion of the bottoms stream is cooled in the second heat exchanger 3 by exchange against the feed stream and is then admixed with the first portion of the bottoms stream. This recombined bottoms stream is carried by line 13. A hydrogen stream carried by line 24 is admixed into the bottoms stream, and the bottoms stream continues through line 25. The temperature of this stream is then monitored by a temperature sensor and control means 12 which generates a signal carried by means 11 to the flow control valve 10. This signal is based on a comparison of actual temperature of the cooled bottoms stream to the then desired reaction zone inlet temperature which is performed by means 12.

The bottoms stream emerges from the reaction zone as an effluent stream carried by line 15. This effluent stream is also divided into two portions. A first portion carried by line 18 is cooled in the first heat exchange means 2 and a second portion is passed around this heat exchange means through line 19 at a rate controlled by valve means 20. The two portions of the reaction zone effluent stream are then combined and passed through a temperature sensing and control means 23 in line 22. This control means generates a signal carried to valve 20 by means 21 which is indicative of the difference between the instantaneous temperature of the recombined reaction zone effluent stream and its desired temperature. Valve 20 is adjusted in response to this signal to correct the ratio of the flow rates of two portions of the reaction zone effluent stream. The reaction zone effluent stream is then passed to a downstream zone, such as a vapor-liquid separation zone or a fractionation column.

Required subsystems and assemblies such as pumps, pressure control systems, reboilers, condensers and fractionator internals have been deleted for the purposes of simplicity and clarity. This description of one mode of the preferred embodiment is not intended to limit the scope of the invention or to limit its practice to this mode of operation. As indicated below, various modifications to the control system, reaction system and fractionation train may be made while still retaining the operational characteristics of the invention.

DETAILED DESCRIPTION

Low or moderate temperature catalytic reaction zones are used in a wide variety of processes in the petroleum and petrochemical industries. The materials which are beneficially affected by this operation range from lube oils and benzene to pharmaceutical products and normal paraffins. The clay treating operation described in detail in my prior applications is one example of such a process. Mild hydrotreating operations used to remove sulfur or nitrogen compounds or to saturate olefinic hydrocarbons contained in a feed stream are other examples. The isomerization of various hydrocarbons including olefins, paraffins and aromatics may also be performed at relatively low or moderate temperatures.

The exact temperature desired for operation of a reaction zone is dependent on at least three separate factors. The first of these is the minimum temperature which is required for the catalyst to function properly. This temperature normally increases in a positive relation to the quantity of hydrocarbons which has been treated per unit mass of contact material. The preferred inlet temperature of the reaction zone is therefore affected by the prior use of the catalyst. A second factor is the particular type of catalyst which is being used. This is related to the minimum required temperature, but is an independent factor since individual catalysts exhibit differing degrees of selectivity and other properties, such as useful life, which must be taken into account. For instance, at the same temperature and level of conversion, two different catalysts may have different selectivities for the desired reaction. Finally, the optimum hydrocarbon conversion temperature will be dependent on intrinsic and extrinsic qualities of the hydrocarbon stream being treated. These qualities include the rate of flow of the hydrocarbon stream and the concentration of impurities which are to be removed. The type of process being performed will also be a material factor. For instance, the optimum temperature for use in a hydrogenation process may well differ from that for use in a hydrodesulfurization process. For these and other reasons, it is normally necessary to adjust the preselected temperature at which the reaction zone is maintained during the operation of the process.

In a large number of hydrocarbon conversion processes, the hydrocarbons forming the feed stream fed to the reaction zone are removed from a fractionation column. This column may be utilized as a stripper or splitter as a feed preparation operation. In other processes, this fractionator may be a product finishing step used in conjunction with an upstream reaction zone. It is highly probable that during the time the process in on-stream, the operating conditions of the fractionation column will vary. This will include both short-term fluctuations resulting from minor changes in the temperature or composition of the material fed to the fractionator and longterm fluctuations resulting from changes in catalyst activities, desired product specifications, etc. It is therefore desirable to be able to adjust the temperature of the fractionation column effluent stream before it is fed into the reaction zone to thereby prevent erratic operation of the reaction zone.

The high probability of fluctuations in the operation of the fractionation column which is producing the stream fed to the reaction zone makes it preferable to use a control system which is not dependent on the control system of the fractionation column. Furthermore, operation of the reaction zone at a higher temperature than the upstream fractionator requires the reaction zone feed stream to be heated to this elevated temperature. This in turn requires the use of a separate heater and heat source, an undesirable requirement. Another consideration in the design of the process is that the effluent of the reaction zone is often passed into a fractionation column or other processing unit which it is desired to charge a feed stream having a constant temperature. It is therefore desirable to have a system for modifying and controlling the temperature of the reaction zone effluent stream.

It is therefore an objective of this invention to provide a control system and a method for controlling at a preselected temperature a hydrocarbon stream which has been removed from a fractionation column and is being passed into a reaction zone. It is another objective to provide an integrated flow and temperature control system and a method for its use on the bottoms stream of a stripping column which eliminates the need to heat the bottoms stream before passage into a reaction zone and which recovers heat from the reaction zone effluent stream to minimize the reboiler duty of the stripping column. It is yet another objective to provide an integrated fractionation and hydrocarbon conversion method wherein the effluent of a reaction zone is passed into a fractionation column or other downstream unit at a substantially constant temperature despite changes in the reaction zone inlet temperature. It is another objective of the invention to provide a method of adjusting the temperature of hydrocarbon feed stream entering the upstream fractionator while simultaneously adjusting the temperature of the fractionator effluent stream which is entering a reaction zone.

These objectives are met by the subject method, which includes operating the fractionation column at an increased pressure which requires the use of a bottoms temperature greater than the maximum reaction zone inlet temperature which will be used. This high bottoms temperature is maintained constant, preferably by a control system regulating the operation of the reboiler. The next step in the method is to cool the fractionation column bottoms stream by the unique operation of bifurcating the bottoms stream and then heat exchanging one portion of it against the relatively cool material being charged into the fractionation column. The amount of this portion will vary with such changeable factors as the instantaneous preselected reaction zone inlet temperature, the temperature of the feed to the fractionation column, and the temperature and flow rate of the bottoms stream itself. For instance, as the activity of the catalyst in the reaction zone decreases and the preselected temperature is gradually increased to compensate, the flow rate of the cooled portion of the bottoms stream will be adjusted downward to raise the reaction zone inlet temperature. The flow rate of the cooled portion would also be decreased if the temperature of the fractionation column feed stream decreases.

Although the fractionation column could be maintained at a temperature which would not require cooling of the bottoms stream even when the reaction zone is operated at its maximum desired inlet temperature, it is preferred that a higher temperature is maintained in the column such that some cooling of the bottoms stream is required at all times. This makes control of the temperature more stable and allows room for adjustment. Specifically, it is preferred that the bottom temperature of the column is set at least 15° F. above the maximum foreseeable desired inlet temperature for the reaction zone. Furthermore, it is preferred that at all times at least 5-10 wt.% of the bottoms stream is split off for heat exchange. The maximum amount of the bottoms stream which is split off and cooled is preferably less than 50 wt.% but may be higher. In a like manner it is preferred that at all times at least 5-10 wt.% of the reaction zone effluent stream is bypassed around the first heat exchanger through line 19. However, the maximum amount of the reaction zone effluent stream which is bypassed is preferably in the order of about 70 wt.%.

While this description is given in terms of passing a stripping column bottoms stream though a reaction zone, it is not intended to limit the scope of the invention to this preferred embodiment. The subject method may be applied to other streams, such as side-cut streams, which are withdrawn at the proper temperature. It may also be applied to the bottom streams of columns not properly referred to as stripping columns. The design and other operational aspects of the fractionation column may be as is customary and established in the art.

After being cooled, the split-off portion of the bottoms stream is admixed with the uncooled portion of the bottoms stream and the temperature of the resultant stream is measured. This temperature is compared to the reaction zone inlet temperature which is desired at this point in time, and the control valve which is regulating the division of the bottoms stream is then adjusted as needed to bring the measured temperature to the desired temperature. The control valve, heat exchanger, and temperature sensing and control means used for this may be any of the conventional devices known to those skilled in the art. All of the control system components are preferably utilized as shown in the drawing. That is, the rate of the bottoms stream division is preferably set by a control valve in the transfer line carrying the uncooled portion of the bottoms stream, and the rate of flow of the total bottoms stream is preferably regulated by a level control means which signals a control valve in the transfer line carrying the total reaction zone effluent. This control valve may be in either line 15 or line 22. Other systems may be used to practice the method of the invention. For instance, the flow rate of the total bottoms stream may be regulated by a valve means in line 13 or the temperature of the resulting admixture could be determined by computations based on flow rate and temperature measurements of both portions of the bottoms stream. Other possible variations include using a temperature measured within the reaction zone or the temperature of the reaction zone effluent stream to control the cooling of the fractionation column bottoms stream.

The reaction zone may be of any type and configuration which is effective in achieving the desired degree of conversion. It may utilize either upward or downward flow, with downward flow being preferred. The reaction zone is maintained at hydrocarbon conversion conditions suitable for the specific process which is being performed. These processes may comprise reforming, isomerization, hydrotreating, alkylation, transalkylation, etc. The reaction zone will be maintained at what may be referred to as a low or moderate temperature since the maximum temperature which is used in a fractionation column is often limited by such factors as the thermal stability of the feed stream. Furthermore, liquid phase material must be present in the fractionation column and this limits the temperature which may be used in the column at any one pressure. It is therefore preferred to operate the reaction zone at a temperature of from about 250° F. to about 650° F.

The hydrocarbon conversion conditions will also preferably comprise a positive but moderate pressure. This is because of the tremendous expense of building high pressure fractionation columns combined with the preference for the maintenance of a higher pressure in the fractionation column than in the reaction zone. Such a pressure differential eliminates the need for a separate pumping system and thereby holds down the capital cost of the process. The higher pressure in the column is also conductive to the desired high temperature fractionation. Therefore, although higher pressures could be used, it is preferred that the hydrocarbon conversion conditions utilized in the reaction include a pressure within the range of about 25 to 550 psig. The other conditions, such as the space velocity of the reactants, etc., may be those which are customarily used with the specific desired reaction. A broad range of preferred liquid hourly space velocities extends from about 0.8 to 5.0.

The action of the fractionation column on the feed stream will result in the fractionation column effluent stream which is fed to the reaction zone being essentially free of hydrogen. In a great many hydrocarbon conversion processes, it is necessary or desired for hydrogen to be present in the reaction zone. This may be for several reasons, such as increasing the useful life of the catalyst or supplying the hydrogen consumed in the reaction. The subject process may be adapted to the passage of hydrogen into the reaction zone in several ways. For example, the added hydrogen stream could be independently heated to the desired inlet temperature of the reaction zone prior to the admixture of hydrogen stream with the fractionation column effluent stream. As an alternative, the hydrogen stream may be admixed with the fractionation column effluent stream prior to the measurement of the temperature of the fractionation column effluent stream. This allows the control system to also compensate for changes in the temperature or flow rate of the hydrogen stream and is the preferred method. The rate of hydrogen addition will vary widely depending on many factors. During very mild hydrotreating, the quantity of added hydrogen may be small enough that it dissolves in the lean hydrocarbon liquid being charged to the reactor. At higher hydrogen addition rates, two-phase flow will result. In such mixed-phase hydrocarbon conversion processes the mixed-phase reaction zone effluent stream is normally cooled and passed into a vapor-liquid separation zone. The effluent of the process carried by line 22 may therefore be directed into a separatory vessel from which unconsumed hydrogen is recovered for recycling. The effluent of the process may also be directed into a different unit operation such as a second fractionation column or a second reaction zone.

The reaction zone will contain a catalytically effective composite comprising an active component. For hydrotreating, this active component may be a metal or an oxide of a metal selected from Groups VIII or VI-B of the Periodic Table or a combination of these metals. The active component of the catalyst is deposited on or admixed with an inorganic oxide support such as silica or alumina. A preferred hydrotreating catalyst comprises nickel and cobalt on an alumina-silica support. The alumina is preferably present in greater proportions, with the weight ratio of alumina to silica being from about 1.5:1 to 9:1, and preferably 1.5:1 to 3:1. The catalyst used is subject to much variation and could be a sulfided cobalt-molybdenum-alumina catalyst, etc. Other possible carrier materials include zirconia, titania, bauxite or bentonite. A commercially available catalyst may be used in the reaction zone for hydrotreating or for other processes.

Hydrotreating is normally performed at a liquid hourly space velocity of about 1 to 5, a pressure of about 100 to 1200 psig. and a temperature of from about 300° F. to 750° F. These conditions will preferably be adjusted to more moderate conditions set out above. Hydrogen is circulated through the reaction zone at a rate of about 500 to 6,000 standard cubic feet per barrel (SCFB) of feed hydrocarbons. About 200 to 1000 SCFB of hydrogen is normally consumed. The severity of the hydrotreating operation will be adjusted in accordance with the specific goal of the operation, the composition of the feed stream, activity of the catalyst, etc. Further details on hydrotreating processes may be obtained by referring to such references as U.S. Pat. Nos. 3,726,788; 3,537,982 and 2,767,121.

Isomerization conditions preferably include a temperature in the range from about 200° F. to about 650° F. and higher, but are subject to the previously described constraints. Preferred isomerization conditions also include a pressure of from about 25 to 550 psig. Hydrogen or other gases and catalyst promoters may also be charged to the reaction zone. Hydrogen is preferably charged at the rate of about 0.25–10.0 moles of added hydrogen per mole of hydrocarbon to be isomerized. The reaction zone is preferably operated at a liquid hourly space velocity (volume of hydrocarbons at standard conditions charged per hour divided by the volume of catalyst in the reaction zone) of from about 0.5 to 10.0. Operation outside of these ranges is also possible. The catalysts described in the previously listed references or other commercially available catalysts may be used in the isomerization zone.

A portion of the effluent of the reaction zone is heat exchanged with the feed stream being charged to the fractionation column. This has two beneficial results. First, it recovers a sizable amount of heat and reduces the column's reboiler duty. Second, by regulating the performance of the heat exchange as described herein, the temperature of the reaction zone effluent stream may be adjusted to a desired inlet temperature of the downstream operation or vessel, thus smoothing the operation of the downstream operation.

There are two other advantages to the high temperature fractionation operation used in the subject invention. First, the recovery of heavier components, such as benzene, in the bottoms stream of a stripping column is greater than at a lower pressure and temperature. Second, the overhead vapors of the column are at higher temperatures which allow more efficient utilization of their heat content. For instance, they can be used to generate steam or as a heating fluid for the reboiler of another column. While these two advantages to high temperature operation have been known for some time, the synergy of their benefits with those of the invention overcome the disadvantages of high temperature operation.

In accordance with the above description, the preferred embodiment of my invention may be characterized as a process for controlling the temperature of a stripping column bottoms stream as it is being passed into a reaction zone and of adjusting the temperature of the reaction zone effluent stream which comprises the steps of passing a hydrocarbon feed stream comprising $C_2$ to $C_8$ hydrocarbons into a stripping column operated at effective fractionation conditions including a bottom temperature above a maximum desired inlet temperature of a downstream reaction zone and effecting the removal of $C_2$ to $C_5$ hydrocarbons from the hydrocarbon feed stream by fractionation to thereby produce a stripping column bottoms stream having a first temperature which is above an instantaneous preselected inlet temperature for the reaction zone; cooling the stripping column bottoms stream to a second temperature by dividing the stripping column bottoms stream into a first portion and a second portion, cooling the second portion by indirect heat exchange against the hydrocarbon feed stream, recombining the first portion and the second portion of the stripping column bottoms stream and admixing a hydrogen stream into the stripping column bottoms stream; measuring the second temperature of the stripping column bottoms stream, and comparing the second temperature to the instantaneous preselected inlet temperature for the reaction zone; adjusting the relative flow rates of the first portion and the second portion of the stripping column bottoms stream in a manner which changes the second temperature of the stripping column bottoms stream to the instantaneous preselected inlet temperature of the reaction zone; passing the stripping column bottoms stream through the reaction zone at hydrocarbon conversion conditions to produce a reaction zone effluent stream having a first temperature; cooling the reaction zone effluent stream to a second temperature by dividing the reaction zone effluent stream into a first portion and a second portion, cooling the second portion by indirect heat exchange against the hydrocarbon feed stream, and then recombining the first portion and the second portion of the reaction zone effluent stream; measuring the second temperature of the reaction zone effluent stream, and comparing the second temperature to the instantaneous preselected inlet temperature of a downstream unit operation; adjusting the relative flow rates of the first portion and the second portion of the reaction zone effluent stream in a manner which changes the second temperature of the reaction zone effluent stream to the instantaneous preselected inlet temperature of the downstream unit operation.

In a different embodiment of the invention, the temperature measurement and control means 23 shown in line 22 of the drawing is moved to line 1. Preferably, it is placed downstream of the second heat exchanger 3. In this embodiment, the portion of the reaction zone effluent stream which is passed through line 19, and therefore not cooled, is adjusted in a manner which changes the measured or actual temperature of the hydrocarbon feed stream to the then preselected inlet temperature of the stripping column 4. This method may be used to compensate for changes in the amount of heat delivered to the feed stream by the relatively hot stripping column bottoms material passing through line 8. It is also preferred that the sequence of heat exchange steps performed in heat exchangers 2 and 3 be in the order illustrated in the drawing. As an alternative, the hydrocarbon feed stream may be first heat exchanged with the second portion of the stripper bottoms stream and then heat exchanged with the second portion of the reaction zone effluent stream.

I claim as my invention:

1. A method for controlling the temperature of a fractionation column effluent stream as the effluent stream is being passed into a hydrotreating reaction zone and of adjusting the temperature of the hydrotreating reaction zone effluent stream which comprises the steps of:

(a) passing a hydrocarbon feed stream which comprises $C_2$ to $C_8$ hydrocarbons into a fractionation column operated at effective fractionation conditions including a bottom temperature above a maximum desired inlet temperature of a downstream hydrotreating reaction zone, and effecting the removal of $C_2$ to $C_5$ hydrocarbons from the hydrocarbon feed stream by fraction to thereby produce a fractionation column effluent stream having a first temperature which is above an instantaneous preselected inlet temperature for said reaction zone;

(b) cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;

(c) measuring the second temperature of the fractionation column effluent stream, and comparing the second temperature to the instantaneous preselected inlet temperature for said reaction zone;

(d) adjusting the relative flow rates of the first portion and the second portion of the fractionation column effluent stream in a manner which changes the second temperature of the fractionation column effluent stream to the instantaneous preselected inlet temperature for said reaction zone;

(e) passing the fractionation column effluent stream through said reaction zone at hydrocarbon conversion conditions to produce a hydrotreating reaction zone effluent stream having a first temperature;

(f) cooling said reaction zone effluent stream to a second temperature by dividing said reaction zone effluent stream into a first portion and a second portion, cooling the second portion by indirect heat exchange against the hydrocarbon feed stream, and then recombining the first portion and the second portion of said reaction zone effluent stream;

(g) measuring the second temperature of said reaction zone effluent stream, and comparing the second temperature to the instantaneous preselected inlet temperature of a downstream unit operation; and, (h) adjusting the relative flow rates of the first portion and the second portion of said reaction zone effluent stream in a manner which changes the second temperature of said reaction zone effluent stream to the instantaneous preselected inlet temperature of the downstream unit operation.

2. The method of claim 1 further characterized in that the fractionation column effluent stream is the bottoms stream of the fractionation column.

3. The method of claim 2 further characterized in that a hydrogen stream is admixed with and cools the bottoms stream of the fractionation column before the temperature measurement of step (c) is performed.

4. A method for controlling the temperature of a fractionation column effluent stream as the effluent stream is being passed into a hydrotreating reaction zone and of adjusting the temperature of the hydrocarbon stream being fed to the fractionator column which comprises the steps of:
  (a) measuring the existing temperature of a hydrocarbon feed stream which comprises $C_2$ to $C_8$ hydrocarbons as the hydrocarbon feed stream is being passed into a fractionation column operated at effective fractionation conditions including a bottom temperature above a desired inlet temperature of a downstream hydrotreating reaction zone, and effecting the removal of $C_2$ to $C_5$ hydrocarbons from the hydrocarbon feed stream by fractionation to thereby produce a fractionation column effluent stream having a first temperature which is above an instantaneous preselected inlet temperature for said hydrotreating reaction zone;
  (b) cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;
  (c) measuring the second temperature of the fractionation column effluent stream, and comparing the second temperature to the instantaneous preselected inlet temperature for said reaction zone;
  (d) adjusting the relative flow rates of the first portion and the second portion of the fractionation column effluent stream in a manner which changes the second temperature of the fractionation column effluent stream to the instantaneous preselected inlet temperature for said reaction zone;
  (e) passing the fractionation column effluent stream through said reaction zone at hydrocarbon conversion conditions to produce a hydrotreating reaction zone effluent stream;
  (f) dividing said reaction zone effluent stream into a first portion and a second portion, heat exchanging the second portion against the hydrocarbon feed stream and thereby heating the hydrocarbon feed stream, and then recombining the first portion and the second portion of said reaction zone effluent stream;
  (g) comparing the existing temperature of the hydrocarbon feed stream to a preselected inlet temperature for the hydrocarbon feed stream; and,
  (h) adjusting the relative flow rates of the first portion and the second portion of said reaction zone effluent stream in a manner which changes the existing temperature of the hydrocarbon feed stream as determined in step (a) to the preselected inlet temperature of the hydrocarbon feed stream entering the fractionation column.

5. The method of claim 4 further characterized in that the hydrocarbon feed stream is first heat exchanged against the second portion of the reaction zone effluent stream and is then heat exchanged against the second portion of the fractionation column effluent stream.

6. A method for controlling the temperature of a fractionation column effluent stream as the effluent stream is being passed into an isomerization reaction zone and of adjusting the temperature of an isomerization reaction zone effluent stream which comprises the steps of:
  (a) passing a hydrocarbon feed stream which comprises $C_2$ to $C_8$ hydrocarbons into a fractionation column operated at effective fractionation conditions including a bottom temperature above a maximum desired inlet temperature of a downstream isomerization reaction zone, and effecting the removal of $C_2$ to $C_5$ hydrocarbons from the hydrocarbon feed stream by fractionation to thereby produce a fractionation column effluent stream having a first temperature which is above an instantaneous preselected inlet temperature for said reaction zone;
  (b) cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;
  (c) measuring the second temperature of the fractionation column effluent stream, and comparing the second temperature to the instantaneous preselected inlet temperature for said reaction zone;
  (d) adjusting the relative flow rates of the first portion and the second portion of the fractionation column effluent stream in a manner which changes the second temperature of the fractionation column effluent stream to the instantaneous preselected inlet temperature for said reaction zone;
  (e) passing the fractionation column effluent stream through said reaction zone at hydrocarbon conversion conditions to produce an isomerization reaction zone effluent stream having a first temperature;
  (f) cooling said reaction zone effluent stream to a second temperature by dividing said reaction zone effluent stream into a first portion and a second portion, cooling the second portion by indirect heat exchange against the hydrocarbon feed stream, and then recombining the first portion and the second portion of said reaction zone effluent stream;
  (g) measuring the second temperature of said reaction zone effluent stream, and comparing the second temperature to the instantaneous preselected inlet temperature of a downstream unit operation; and,
  (h) adjusting the relative flow rates of the first portion and the second portion of said reaction zone effluent stream in a manner which changes the second temperature of said reaction zone effluent stream to the instantaneous preselected inlet temperature of the downstream unit operation.

7. A method for controlling the temperature of a fractionation column effluent stream as the effluent stream is being passed into an isomerization reaction zone and of adjusting the temperature of the hydrocarbon stream being fed to the fractionator column which comprises the steps of:

(a) measuring the existing temperature of a hydrocarbon feed stream which comprises $C_2$ to $C_8$ hydrocarbons as the hydrocarbon feed stream is being passed into a fractionation column operated at effective fractionation conditions including a bottom temperature above a desired inlet temperature of a downstream isomerization reaction zone, and effecting the removal of $C_2$ to $C_5$ hydrocarbons from the hydrocarbon feed stream by fractionation to thereby produce a fractionation column effluent stream having a first temperature which is above an instantaneous preselected inlet temperature for said isomerization reaction zone;

(b) cooling the fractionation column effluent stream to a second temperature by dividing the fractionation column effluent stream into a first portion and a second portion, cooling the second portion by indirect heat exchange against the hydrocarbon feed stream, and then recombining the first portion and the second portion of the fractionation column effluent stream;

(c) measuring the second temperature of the fractionation column effluent stream, and comparing the second temperature to the instantaneous preselected inlet temperature for said reaction zone;

(d) adjusting the relative flow rates of the flow portion and the second portion of the fractionation column effluent stream in a manner which changes the second temperature of the fractionation column effluent stream to the instantaneous preselected inlet temperature for said reaction zone;

(e) passing the fractionation column effluent stream through said reaction zone at hydrocarbon conversion conditions to produce an isomerization reaction zone effluent stream;

(f) dividing said reaction zone effluent stream into a first portion and a second portion, heat exchanging the second portion against the hydrocarbon feed stream and thereby heating the hydrocarbon feed stream, and then recombining the first portion and the second portion of said reaction zone effluent stream;

(g) comparing the existing temperature of the hydrocarbon feed stream to a preselected inlet temperature for the hydrocarbon feed stream; and, (h) adjusting the relative flow rates of the first portion and the second portion of said reaction zone effluent stream in a manner which changes the existing temperature of the hydrocarbon feed stream as determined in step (a) to the preselected inlet temperature of the hydrocarbon feed stream entering the fractionation column.

* * * * *